US010113960B2

(12) United States Patent
Kamrat

(10) Patent No.: US 10,113,960 B2
(45) Date of Patent: Oct. 30, 2018

(54) ARRANGEMENT IN CONNECTION WITH MEASURING WINDOW OF REFRACTOMETER, AND REFRACTOMETER

(71) Applicant: JANESKO OY, Vantaa (FI)

(72) Inventor: Esko Kamrat, Vantaa (FI)

(73) Assignee: JANESKO OY, Vantaa (FI)

( * ) Notice: Subject to any disclaimer, the term of this patent is extended or adjusted under 35 U.S.C. 154(b) by 0 days.

(21) Appl. No.: 15/193,669

(22) Filed: Jun. 27, 2016

(65) Prior Publication Data
US 2016/0377538 A1   Dec. 29, 2016

(30) Foreign Application Priority Data
Jun. 29, 2015 (FI) ...................................... 20155513

(51) Int. Cl.
G01N 21/43 (2006.01)

(52) U.S. Cl.
CPC ....... G01N 21/43 (2013.01); G01N 2021/434 (2013.01)

(58) Field of Classification Search
CPC ......................... G01N 21/43; G01N 2021/434
See application file for complete search history.

(56) References Cited

U.S. PATENT DOCUMENTS

| 1,539,579 | A |   | 5/1925 | Stanislaus |
| 4,451,147 | A | * | 5/1984 | Dobes ................... G01N 21/43 |
|           |   |   |        | 356/135 |
| 4,571,075 | A |   | 2/1986 | Kamrat |

(Continued)

FOREIGN PATENT DOCUMENTS

DE          33 14 770 A1    10/1984
DE   10 2007 039 349 A1     2/2009
(Continued)

OTHER PUBLICATIONS

Office Action dated Nov. 18, 2016, by the Finnish Patent Office in corresponding Finnish Patent Application No. 20155513. (7 pages).

(Continued)

Primary Examiner — Shawn Decenzo
(74) Attorney, Agent, or Firm — Buchanan Ingesoll & Rooney PC

(57) ABSTRACT

An exemplary arrangement includes a prism-shaped measuring window, which has a measuring surface adapted to contact a substance being measured. A first surface is adapted to direct light originating from a light source to the measuring surface through the measuring window. A second surface is adapted to direct totally reflected light from an interface between the measuring surface in contact with the substance being measured and a substance being measured outside of the measuring window. A first lens arrangement is adapted to focus the light from the light source on the first surface. A second lens arrangement is adapted to focus the totally reflected light passing through the second surface to a device used for analysis. A lens in each of the first and second lens arrangements closest to the measuring window is integrated into the measuring window and establishes optical refractive power in the first and second surfaces.

5 Claims, 1 Drawing Sheet

(56) References Cited

U.S. PATENT DOCUMENTS

| | | | |
|---|---|---|---|
| 4,803,470 A | 2/1989 | Fineman | |
| 5,309,288 A | 5/1994 | Kahre | |
| 5,323,637 A | 6/1994 | Bendicks et al. | |
| 5,572,315 A | 11/1996 | Krell | |
| 6,067,151 A | 5/2000 | Salo | |
| 6,396,576 B1* | 5/2002 | Bleyle | G01N 21/43 356/128 |
| 6,760,098 B2 | 7/2004 | Salo | |
| 7,619,723 B2 | 11/2009 | Salo | |
| 8,542,353 B2* | 9/2013 | Christian | G01N 21/43 356/128 |
| 2002/0159050 A1 | 10/2002 | Sharma et al. | |
| 2003/0169417 A1 | 9/2003 | Atkinson et al. | |
| 2003/0193663 A1 | 10/2003 | Hong et al. | |
| 2004/0075827 A1 | 4/2004 | Byrne | |
| 2006/0238766 A1 | 10/2006 | Polwart | |
| 2010/0025112 A1* | 2/2010 | Sroka | G01N 21/43 175/49 |
| 2011/0188030 A1 | 8/2011 | Verschuren et al. | |
| 2012/0081698 A1 | 4/2012 | Christian et al. | |
| 2013/0330230 A1* | 12/2013 | Uri | G01N 21/658 422/69 |
| 2015/0069223 A1 | 3/2015 | Yoshimura | |

FOREIGN PATENT DOCUMENTS

| | | |
|---|---|---|
| EP | 0 359 167 A2 | 3/1990 |
| JP | 2000019110 A | 1/2000 |
| JP | 2003215035 A | 7/2003 |

OTHER PUBLICATIONS

Finnish Search Report dated Dec. 15, 2015 for Application No. 20155513.

Office Action dated Mar. 2, 2018 in corresponding Finnish Patent Application No. 20155513.

* cited by examiner

ARRANGEMENT IN CONNECTION WITH MEASURING WINDOW OF REFRACTOMETER, AND REFRACTOMETER

RELATED APPLICATION

This application claims priority under 35 U.S.C. § 119 to Finnish Patent Application No. 20155513 filed in Finland on Jun. 29, 2015, the entire content of which is hereby incorporated by reference.

FIELD

The exemplary embodiments described herein relate to an arrangement in connection with a measuring window of a refractometer, and to a refractometer that has the arrangement described in the above in connection with its measuring window.

BACKGROUND

The operating principle of the refractometer has been known for more than one hundred years. These days, refractometers are used in many fields. For example, refractometers are used in the food industry, wood-processing industry, chemical industry, and various types of research activities.

A refractometer measures the refractive index of a solution in an optical window by means of the total reflection created at the interface between the measuring surface in the measuring window and the solution being measured. A beam of rays from a light source is directed to the interface between the measuring window and the solution being measured. A part of the beam of rays is entirely reflected off the solution, a part is partially absorbed into the solution. This creates an image in which the location of the boundary between the light and dark areas depends on the critical angle of the total reflection, so therefore on the refractive index of the solution.

Known refractometer implementations are described in closer detail in several publications, such as U.S. Pat. Nos. 6,067,151, 6,760,098, and 7,619,723, for example.

In known implementations, the measuring window of a refractometer has been prism-like. The entrance surface, measuring surface, and exit surface of the beam of light have been plane surfaces. To focus light, separate optical components, lenses, have been used. Due to the light passing through a plurality of optical surfaces, reflections are created, and because optical surfaces are not optimal, blurring is also created.

When light arrives from an optically denser substance to an optically less dense substance through a plane surface, the arriving beam of rays is expanded so that the rays arriving against the plane surface at the largest angle are refracted the most. This causes non-linearity in the angular distribution and refractive index measurement of light.

It is known that the numerical aperture remains the same when light travels from one material to another through successive surfaces unless the interfaces have optical refractive power. In a measuring window in which light travels through plane surfaces which thus do not have optical refractive power, the numerical aperture is the same for the rays entering the prism and those exiting it. The specified numerical aperture is defined from the measured refractive index area and the refractive index of the material of the measuring window from the formula $$NA = n_i \sin\theta,$$

where $n_i$ is the refractive index of the material of the measuring window and $\theta$ is the angle between the middle ray and edge ray or the measurement area.

A refractometer measurement involves the analysis of the image created by the reflection of light. The purpose of the image analysis is to find the critical angle of the total reflection, which is the boundary where a light area of an image formed as described in the above turns into a dark area.

From at least U.S. Pat. Nos. 4,571,075 and 5,309,288 it is known to manufacture the measuring window of a refractometer in the shape of a prism, where all the surfaces met by light are plane surfaces. Furthermore, EP 0 359 167 known solution in which other geometric forms for the measuring window are used. German publication DE 10 2007 039 349 provides a manufacturing solution that involves measuring the amount of light reflected from the measuring surface so that the measuring window has a Fresnel lens.

It is also known in the field to have the critical angle of the total reflection expressed as a boundary of light and dark areas by directing the light reflected from the interface of the window and liquid by means of a lens system to a cell of a camera, for example. In known devices, the lens system is set to be at a distance of its focal length from the camera. Known refractometers direct light through prism-like surfaces to the interface of the liquid being measured and measuring window. Moreover, known refractometers direct light through prism surfaces serving as mirrors to the liquid interface.

As would be understood from known implementations, the operation of a refractometer is based on a most accurate angular measurement, because the critical angle of the total reflection is determined according to the refractive index of two substances. In known refractometers, problems have arisen, for example, due to the fact that the optics (e.g., lens arrangements) used in connection with the measuring window, and the light detector have been rigidly fixed to the frame structure of the device. Consequently, if the frame structure warps, for example, an error will result in the angular measurement. In the construction of a refractometer, the objective lens on the side of the detection of the critical angle should be as close as possible to the interface between the prism acting as the measuring window and the solution. A prism manufactured with plane surfaces makes the construction of the measuring device problematic. It has proven difficult to mechanically mount the lenses in a lens arrangement so that thermal movement or vibration do not change the place or position of the lenses when very small angular changes are measured. In particular, it is difficult to mount the objective lens in close proximity to the prism, which acts as the measuring window, in an adequately stable manner.

SUMMARY

An arrangement in connection with a measuring window of a refractometer is disclosed, the arrangement comprising: a prism-shaped measuring window, which has a measuring surface adapted to contact a substance being measured; a first surface through which light originating from a light source is adapted to be directed to the measuring surface through the prism-shaped measuring window; a second surface, through which totally reflected light from an interface between the measuring surface in contact with the substance being measured and the substance being measured, is adapted to be directed outside of the measuring window for analysis; and a first lens arrangement and a second lens arrangement, wherein the first lens arrangement is adapted to focus the light originating from the light source as desired on the first surface, and the second lens arrangement is adapted to focus the totally reflected light passing through the second surface to a device used for analysis, wherein a lens in each of the first and second lens arrangements that is closest in relation to the measuring window is integrated into the measuring window, and surfaces of the lens in each of the first and second lens arrangements is adapted to form the first and second surfaces, respectively, which have optical refractive power, and wherein the lens in each of the first and second lens arrangements that is closest in relation to the measuring window is of a same material as a material of the measuring window and is adapted to form a seamless structure with the measuring window.

BRIEF DESCRIPTION OF THE DRAWINGS

In the following, the invention will be explained in closer detail by means of an exemplary embodiment described in the attached drawing, in which.

DETAILED DESCRIPTION

Figure 1:
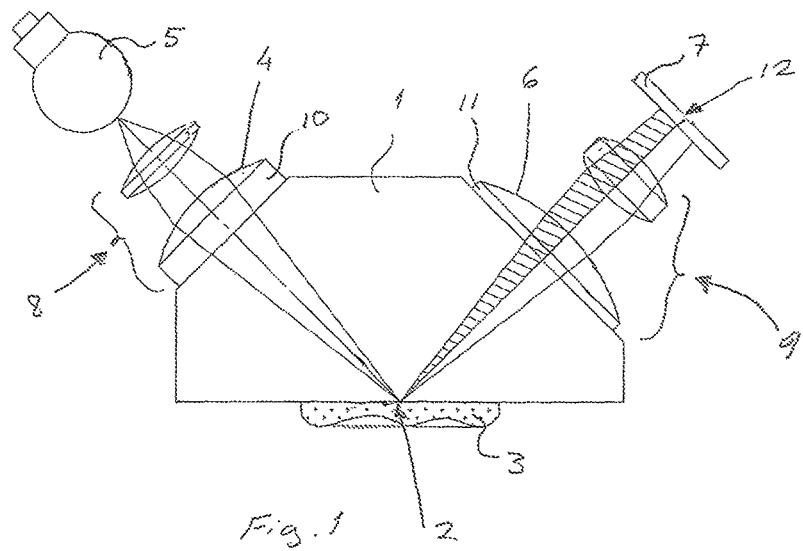
FIG. 1 shows a principle view of an exemplary arrangement from the side in accordance with an exemplary embodiment.

Exemplary embodiments of the present disclosure provide an arrangement in connection with the measuring window of a refractometer and a refractometer, by which the disadvantages of known refractometers can be eliminated. The arrangement in connection with the measuring window of a refractometer described in the present disclosure includes a lens in first and second lens arrangements, which is closest in relation to the measuring window, is integrated into the measuring window, and the surfaces of the lenses of the first and second lens arrangements are adapted to form a first and second surface that have optical refractive power.

Advantages of the exemplary embodiments described herein provide that a numerical aperture is not preserved on the entrance and exit surfaces of light, because these surfaces have optical refractive power. The surfaces of the measuring window, which refract light, may be arranged so that the beams of light used in the measurement at the lighting and detection side are at a narrower angle range than in the case of a measuring window with a plane surface in the corresponding measuring area. So, a narrower angle range and therefore a smaller numerical aperture make it possible to use a simpler lens system. A measuring window where the interfaces have optical refractive power makes it possible to fit the structure of the measuring device in a smaller space. On the other hand, the reason for this is that the quantity of the optical components can be kept low. Secondly, as the beams of light leave the measuring window at a small numerical aperture, allows the use of smaller diameter lenses compared to known refractometer implementations because the beams of light will not disperse at the interface.

According to an exemplary embodiment of the present disclosure, the lens closest to the prism at both sides is integrated into the lens itself, whereby the measuring window is formed of the plane surface acting as the measuring window and of the lens surfaces in the direction of the entering and exiting beams. This way, the quantity of optical surfaces is reduced by four, for example from ten to six.

Because in the arrangement according to the invention, the objective lens is of the same material as the measuring window, mechanical angular changes or those due to temperature cannot take place. For example, by gluing lenses on the surfaces of a prism-like measuring window, good functionality will not be achieved at temperatures exceeding 150° C., because the performance of optical glues does not reach temperatures that high.

Compared to known refractometers, the novel refractometer described in exemplary embodiments of the present disclosure considerably improves the measuring accuracy and stability of refractometer measurements due to its optical and mechanical properties. The physical shape of the measuring window is more unrestricted than in previous solutions, making the construction of the measuring device easier. In particular, problems related to sealing at very high pressures are simpler to solve with the solution according to the invention than with prior art solutions.

According to an exemplary embodiment of the present disclosure, an arrangement includes a prism-shaped measuring window, which has a measuring surface adapted to contact a substance being measured, a first surface through which light originating from a light source is adapted to be directed to the measuring surface through the measuring window, and a second surface through which the totally reflected light from the interface between the measuring surface in contact with the substance being measured and the substance being measured is adapted to be directed outside of the measuring window for analysis, and which arrangement comprises a first and a second lens arrangement, whereby the first leans arrangement is adapted to focus the light as desired on the first surface, and the second lens arrangement is adapted to focus the totally reflected light passing through the second surface to the device used for analysis.

Figure 2:
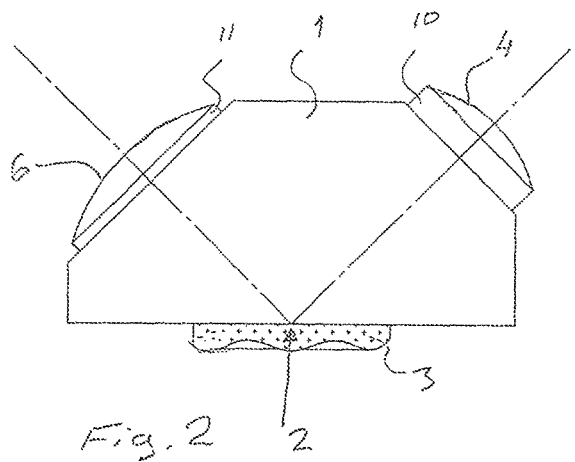
FIG. 2 is a view of the exemplary arrangement of FIG. 1 from an opposite side in accordance with an exemplary embodiment.
Figure 3:
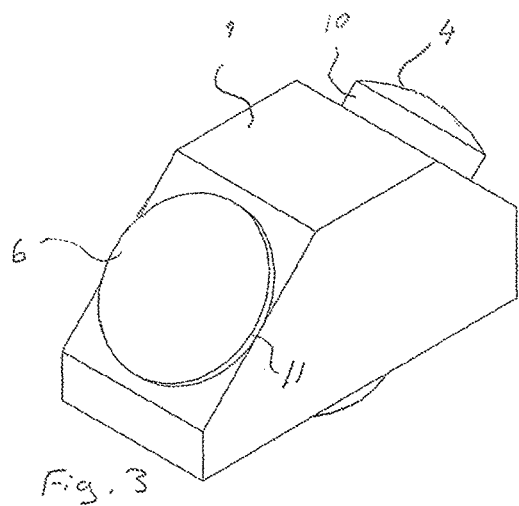
FIG. 3 shows a perspective view of the exemplary arrangements of FIGS. 1 and 2 in accordance with an exemplary embodiment.

FIGS. 1-3 indicate the measuring window of a refractometer with reference number 1. During measurement, the measuring surface 2 of the measuring window 1 of the refractometer is in contact with the substance 3 being measured.

FIG. 1 shows a principle view of an exemplary arrangement from the side in accordance with an exemplary embodiment. FIG. 2 is a view of the exemplary arrangement of FIG. 1 from an opposite side in accordance with an exemplary embodiment. FIG. 3 shows a perspective view of the exemplary arrangements of FIGS. 1 and 2 in accordance with an exemplary embodiment.

As shown in FIGS. 1-3, the measuring window 1 is an element shaped like a prism and the measuring surface 2 is a plane surface.

The measuring window 1 has a first surface through which light from a light source 5 is adapted to be directed to a measuring surface 2 through the measuring window 1 during measurement. The measuring window 1 further has a second surface, through which the totally reflected light from the interface between the measuring surface 2 that is in contact with the substance 3 being measured and the substance being measured is adapted to be directed outside of the measuring window 1 for analysis. The analysis may take place by means of a suitable device 7, such as a light-sensitive surface.

The arrangement shown in the figures also includes a first lens arrangement 8 and a second lens arrangement 9. The first lens arrangement 8 is adapted to focus light as desired on the first surface. The second lens arrangement 9 is adapted to focus the totally reflected light that passes through the second surface onto the device 7 used in the analysis.

An advantageous feature of the exemplary embodiments of the present disclosure includes a lens 10, which is in the first lens arrangement 8 and closest in relation (e.g., proximity) to the measuring window 1, being integrated into the measuring window. An advantage also includes the lens 11, which is in the second lens arrangement 9 and closest in relation to the measuring window 1, being integrated into the measuring window 1. The surfaces of the aforementioned lenses 10, 11 that are closest in relation to the measuring window are adapted to form the first surface 4 and second surface 6, which have optical refractive power.

An additional feature of the arrangement according to an exemplary embodiment of the present disclosure is that the lenses 10, 11 closest in relation to the measuring window 1 are of the same material as the material of the measuring window 1 and are adapted to form a seamless structure with the measuring window 1.

Still further, an advantageous feature provided by the exemplary embodiments described herein includes the first surface 4 of the lens 10, which is closest in relation to the measuring window 1, and the second surface 6 of the lens 11, which is closest in relation to the measuring window 1, are spherical or aspherical surfaces.

The operating principle of the exemplary embodiments of the arrangement illustrated in FIGS. 1-3 is described below.

The measuring window 1 is in physical contact with the liquid 3 being measured. Beams of light are brought from a light source 5 through the first lens arrangement 8 on the first surface 4 of the measuring window 1. The first surface 4 has optical refractive power. The first lens arrangement 8, which includes the surface 4 having optical refractive power, produces the desired angular distribution on the measuring surface 2 of the measuring window. For the measuring window 1, beams of light are brought at such an angle range that it includes the critical angle of the total reflection taking place on the measuring surface.

The critical angle of the total reflection depends on the refractive index of the substance 3 being measured and the measuring window at the wavelength of the light. The refractive index being measured is then obtained by means of the Snell law, provided as $$n = n_i \sin \alpha_c.$$

In the equation above, n is the refractive index of the liquid being measured, $n_i$ is the refractive index of the material of the measuring window, and $\alpha_c$ is the critical angle of the total reflection. The refractive index of the measuring window must always be bigger than that of the substance being measured.

The totally reflected part of the angular distribution passes through the second surface 6 of the measuring window 1, the surface having optical refractive power. The second optical surface 6 and the second lens arrangement 9, which includes the second surface 6, together form an optical system having a focal length at the distance of which the light-sensitive surface of the device 7 used in the analysis of the light is set.

When an image is formed on the aforementioned light-sensitive surface, the boundary 12 between the light and dark areas of the image allows the interpretation of the refractive index of the substance 3 being measured.

The invention is explained above by means of the application example described by the figures. However, the invention is in no way restricted to the accompanying example but may be freely modified within the scope of the claims.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed:

1. An arrangement in connection with a measuring window of a refractometer, the arrangement comprising:
    a prism-shaped measuring window, which has a measuring surface adapted to contact a substance being measured;
    a first surface through which light originating from a light source is adapted to be directed to the measuring surface through the prism-shaped measuring window;
    a second surface, through which totally reflected light from an interface between the measuring surface in contact with the substance being measured and the substance being measured, is adapted to be directed outside of the measuring window for analysis; and
    a first surface normal of the first surface and a second surface normal of the second surface having an intersection point at the interface between the measuring surface in contact with the substance being measured and the substance being measured, the intersection point being adapted to a center point of the measuring surface;
    wherein a totally reflected part of light directed to the measuring surface along the first surface normal is adapted to be directed outside of the measuring window along the second surface normal;
    a first lens arrangement and a second lens arrangement, each of the first lens arrangement and the second lens arrangement including at least two lenses,
    wherein the first lens arrangement is adapted to focus the light originating from the light source on the first surface, and the second lens arrangement is adapted to focus the totally reflected light passing through the second surface to a device used for analysis,
    wherein a lens in each of the first and second lens arrangements that is closest in relation to the measuring window is integrated into the measuring window, and surfaces of the lens in each of the first and second lens arrangements is adapted to form the first and second surfaces, respectively, which have optical refractive power, and
    wherein the lens in each of the first and second lens arrangements that is closest in relation to the measuring window is of a same material as a material of the measuring window and is adapted to form a seamless structure with the measuring window.

2. The arrangement as claimed in claim 1, wherein the first and second surfaces are spherical or aspherical surfaces.

3. A refractometer comprising:
    a measuring window; and
    an arrangement as claimed in claim 1 in connection with the measuring window.

4. A refractometer comprising:
    a measuring window; and
    an arrangement as claimed in claim 2 in connection with the measuring window.

5. An arrangement in connection with a measuring window of a refractometer, the arrangement comprising:
- a triangular prism-shaped measuring window, which has a measuring surface adapted to contact a substance being measured;
- a first surface through which light originating from a light source is adapted to be directed to the measuring surface through the triangular prism-shaped measuring window;
- a second surface, through which totally reflected light from an interface between the measuring surface in contact with the substance being measured and the substance being measured, is adapted to be directed outside of the measuring window for analysis; and
- a first lens arrangement and a second lens arrangement,
- wherein a first lens of the first lens arrangement is adapted to focus the light originating from the light source on the first surface, and a second lens of the second lens arrangement is adapted to focus the totally reflected light passing through the second surface to a device used for analysis,
- wherein a third lens in the first lens arrangement and a fourth lens in the second lens arrangement that are closest in relation to the measuring window are each integrated into the measuring window, and surfaces of the third lens and the fourth lens are adapted to form the first and second surfaces, respectively, which have optical refractive power, and
- wherein the first lens and the third lens are arranged to have a common center axis:
- wherein the second lens and the fourth lens are arranged to have a common center axis;
- wherein the third lens and the fourth lens are of a same material as a material of the measuring window and is adapted to form a seamless structure with the measuring window;
- wherein the second surface and the second lens arrangement including the second surface form an optical system having a focal length at a distance of which a light-sensitive surface of a device used in the analysis is set.

* * * * *